United States Patent

Lee et al.

Patent Number: 6,073,831
Date of Patent: Jun. 13, 2000

[54] ULTRASONIC GENERATOR FOR MINIMIZING HEAT INPUT OF MAGNETOSTRICTIVE ELEMENT AND ITS MANUFACTURING METHOD

[75] Inventors: Yang-Lae Lee; Pil-Woo Heo; Jae heyng Kim; Eui-su Lim, all of Daejeon-Si, Rep. of Korea

[73] Assignee: Korea Institute of Machinery & Metals, Daejeon-Si, Rep. of Korea

[21] Appl. No.: 09/015,610

[22] Filed: Jan. 29, 1998

[30] Foreign Application Priority Data

Nov. 29, 1997 [KR] Rep. of Korea ........................ 97-64661

[51] Int. Cl.[7] .............................. B23K 1/20; H04R 31/00
[52] U.S. Cl. ............................ 228/208; 228/208; 228/226; 29/594; 29/609.1
[58] Field of Search ..................................... 228/190, 225, 228/226, 208; 29/594, 609.1

[56] References Cited

U.S. PATENT DOCUMENTS

| | | | |
|---|---|---|---|
| 2,859,415 | 11/1958 | Fagan | 333/30 |
| 3,149,295 | 9/1964 | Grebe | 333/254 |
| 3,798,746 | 3/1974 | Alphonse et al. | 29/470.1 |
| 3,945,618 | 3/1976 | Shoh | 259/114 |

*Primary Examiner*—Patrick Ryan
*Assistant Examiner*—Lynne Edmondson
*Attorney, Agent, or Firm*—Arent Fox Kintner Plotkin & Kahn, PLLC

[57] ABSTRACT

A method of manufacturing an ultrasonic generator adapted to ultrasonic sterilizers, for minimizing the heat input of a magnetostrictive element, comprises the steps of: forming, on a wave guide, melting layers constructed of joining materials such as Al—Si alloy and Sn—Ag alloy which melt within a temperature range of 575~590° C. and 230~250° C., respectively, and have tensile strength of 17~25 kg/mm$^2$ and 10~15 kg/mm$^2$, respectively; and joining the wave guide with the magnetostrictive element.

4 Claims, 1 Drawing Sheet

ULTRASONIC GENERATOR FOR MINIMIZING HEAT INPUT OF MAGNETOSTRICTIVE ELEMENT AND ITS MANUFACTURING METHOD

BACKGROUND OF THE INVENTION

1. Field of the Invention

The present invention relates to an ultrasonic generator which is necessary for an ultrasonic sterilizer development task, and its manufacturing method. More particularly, it relates to an ultrasonic generator and its manufacturing method which can minimize the heat input of a magnetostrictive element, instead of a furnace heating method under existing pressure conditions, in order to join the magnetostrictive element with a wave guide.

2. Discussion of Related Art

A sterilization treatment is a result of constant devotion to the human health in modern civilized living.

Therefore, there is a necessity for the sterilization in medical care, chemistry, food, electronics, and everyday life.

A conventional chemical sterilization treatment is gradually converted into electronic one due to toxicity of chemical agents itself and poison of residual materials.

In this regard, an ultrasonic sterilizer has been developed.

As shown in FIG. 1, an ultrasonic generator for ultrasonic sterilizer includes a layered magnetostrictive element one, and a wave guide 2 connected to a join surface 3 formed at the front of the magnetostrictive element.

It is necessary that the magnetostrictive element and the wave guide are uniformly and firmly joined to each other with a relatively broad join area over approximately 750 800 mm$^2$.

Considering the magnetic characteristics variation factor of the magnetostrictive element in response to the heat-affection, a joining method for applying less heat input to a joining portion, and the joining materials with proper intensity of joining should be selected.

In a conventional high-temperature furnace heating method, a base metal and the joining materials melt to be welded under pressure conditions, causing the magnetostrictive element to be deteriorated in its ultrasonic sound pressure and durability.

SUMMARY OF THE INVENTION

Accordingly, the present invention is directed to an ultrasonic generator for minimizing heat input of magnetostrictive element and its manufacturing method that substantially obviate one or more of the problems due to limitations and disadvantages of the related art.

An object of the present invention is to provide an ultrasonic generator and its manufacturing method of forming a melting layer on a wave guide, not melting a base metal, before joining a not-preheated magnetostrictive element with the wave guide, instead of melting and welding the base metal and joining materials.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, there is a demand for the joining materials having low melting point and high intensity, and constructed of alloying elements which conform to electric conductivity and wetting property with the base metal.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the invention:

In the drawings:

FIG. 1 schematically illustrates a structure of an ultrasonic generator according to the present invention.

DETAILED DESCRIPTION OF PREFERRED EMBODIMENT

Figure 1:
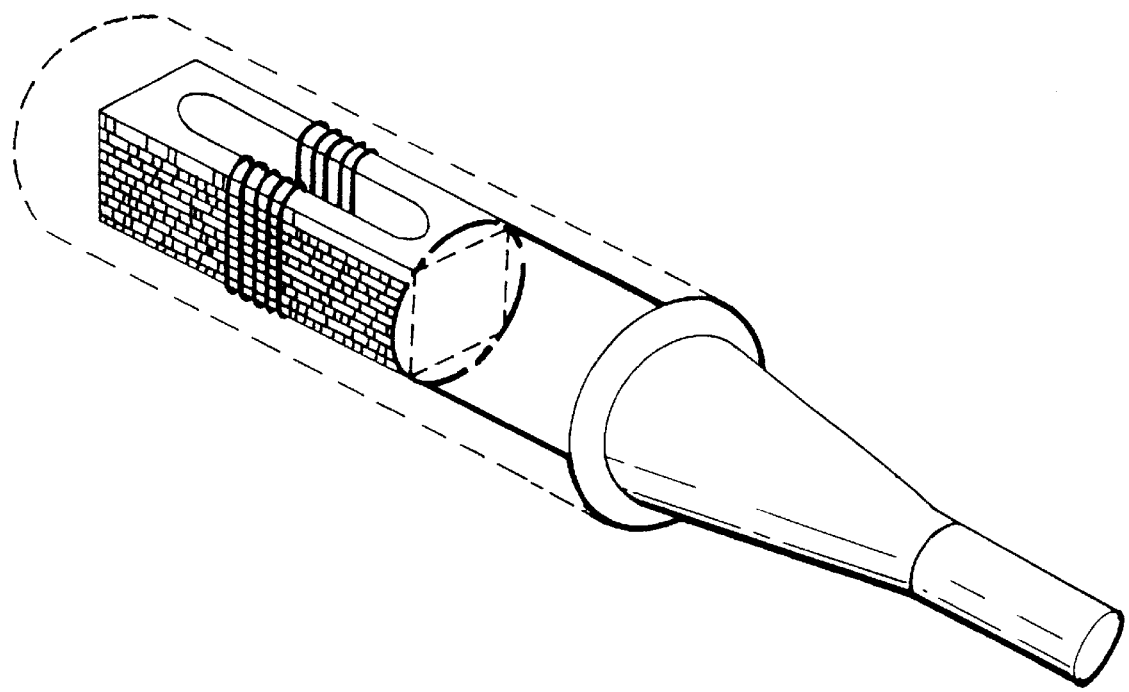

Reference will now be made in detail to the preferred embodiments of the present invention, examples of which are illustrated in the accompanying drawings.

As illustrated in FIG. 1, joining materials such as Al—Si alloy and Sn—Ag alloy are used to make a magnetostrictive element 1 and a wave guide 2 on which a melting layer is formed joined with each other at a join surface 3.

Al—Si alloy melts in a temperature range of 575~590° C. and has tensile strength of 17~25 kg/mm$^2$, and Sn—Ag alloy melts in a temperature range of 230~250° C. and has tensile strength of 10~15 kg/mm$^2$.

Heating method to join the magnetostrictive element with the wave guide is divided into an iron heating method, a gas torch heating method, an electric resistance heating method, an arc heating method, an induction heating method, a furnace heating method and so on.

Among the proper gas torch heating method and induction heating method, the present invention employs the gas torch heating method in order to minimize the heat input of the magnetostrictive element and effectively apply local heat to the joining portion.

Structures and operational principles of the ultrasonic sterilizer, magnetostrictive element, and wave guide are widely known to all. Therefore, the detailed drawing and description thereof will be omitted herein.

The products manufactured according to the present invention have much better ultrasonic sound pressure and durability than those produced by the furnace heating method under pressure conditions. Accordingly, the present invention can be applied to the relevant industries.

It will be apparent to those skilled in the art that various modifications and variations can be made in an ultrasonic generator for minimizing heat input of magnetostrictive element and its manufacturing method of the present invention without departing from the spirit or scope of the invention. Thus, it is intended that the present invention cover the modifications and variations of this invention provided they come within the scope of the appended claims and their equivalents.

What is claimed is:

1. A method of manufacturing an ultrasonic generator adapted to ultrasonic sterilizers, for minimizing the heat input of a magnetostrictive element, comprising the steps of:

forming, on a wave guide, melting layers constructed of joining materials; and joining the wave guide with the magnetostrictive element.

2. A method of manufacturing an ultrasonic generator adapted to ultrasonic sterilizers, for minimizing the heat input of a magnetostrictive element, comprising the steps of:

forming, on a wave guide, melting layers constructed on joining materials; and joining the wave guide with the magnetostrictive element by a gas torch heating method.

3. The method of claim 1, wherein the joining materials are an Al—Si alloy and a Sn—Ag alloy, wherein the Al—Si alloy melts within a temperature range of 575~590° C. and has a tensile strength of 17~25 kg/mm$^2$, wherein the Sn—Ag alloy melts within the temperature range of 230~250° C. and has a tensile strength of 10~15 kg/mm$^2$.

4. The method of claim 2, wherein the joining materials are an Al—Si alloy and a Sn—Ag alloy.

* * * * *